(12) United States Patent
Arndt

(10) Patent No.: US 7,073,666 B2
(45) Date of Patent: Jul. 11, 2006

(54) TAMPON PACKAGE AND METHOD FOR MAKING SAME

(76) Inventor: Jennifer Arndt, 811 Corday Dr., #204, Naperville, IL (US) 60540

( * ) Notice: Subject to any disclaimer, the term of this patent is extended or adjusted under 35 U.S.C. 154(b) by 267 days.

(21) Appl. No.: 10/322,062

(22) Filed: Dec. 17, 2002

(65) Prior Publication Data

US 2004/0112779 A1    Jun. 17, 2004

(51) Int. Cl.
  B65D 81/20    (2006.01)
  B65D 73/00    (2006.01)
  A61B 17/06    (2006.01)

(52) U.S. Cl. .................. 206/524.8; 206/438; 206/440; 206/484

(58) Field of Classification Search ............... 206/363, 206/440, 484, 812, 524.8, 438, 471, 494, 206/38, 446; 604/12, 14, 904
See application file for complete search history.

(56) References Cited

U.S. PATENT DOCUMENTS

| | | | |
|---|---|---|---|
| 3,092,251 A * | 6/1963 | Jaggers ....................... 206/446 |
| 3,152,694 A * | 10/1964 | Nashed et al. .............. 206/440 |
| 3,217,871 A * | 11/1965 | Lee ............................. 206/440 |
| 3,625,348 A * | 12/1971 | Titchenal et al. ........... 206/484 |
| 3,674,029 A | 7/1972 | Bates et al. |
| 3,717,149 A | 2/1973 | Morane |
| 3,749,093 A | 7/1973 | Bloom |
| 3,856,143 A | 12/1974 | Simon et al. |
| 3,982,374 A | 9/1976 | Schaefer |
| 4,056,103 A | 11/1977 | Kaczmarzyk et al. |
| 4,170,305 A | 10/1979 | Hull, Jr. et al. |
| 4,279,344 A * | 7/1981 | Holloway, Jr. ............... 206/484 |
| 4,312,348 A | 1/1982 | Friese |
| 4,373,631 A * | 2/1983 | Friese et al. ................. 206/438 |
| 4,428,747 A | 1/1984 | Friese |
| 4,648,513 A * | 3/1987 | Newman ...................... 383/204 |
| 4,666,833 A | 5/1987 | Roy et al. |
| 4,775,377 A | 10/1988 | Sweere |
| 4,881,644 A | 11/1989 | Norquest et al. |
| 5,133,457 A * | 7/1992 | Kadel .......................... 206/438 |
| 5,180,059 A | 1/1993 | Shimatani et al. |
| 5,891,544 A | 4/1999 | Chappell et al. |
| 5,986,165 A | 11/1999 | Moder et al. |
| 6,068,899 A * | 5/2000 | Osborn et al. .............. 428/35.2 |
| 6,183,456 B1 | 2/2001 | Brown et al. |
| 6,524,269 B1 * | 2/2003 | McNamara ................... 604/12 |
| 6,824,536 B1 * | 11/2004 | Randall et al. .............. 604/904 |
| 2002/0172834 A1 * | 11/2002 | Rivett et al. ................. 206/484 |
| 2003/0029740 A1 * | 2/2003 | Caveness ..................... 206/210 |

* cited by examiner

*Primary Examiner*—Mickey Yu
*Assistant Examiner*—J. Gregory Pickett
(74) *Attorney, Agent, or Firm*—Michael P. Mazza

(57) ABSTRACT

A sealed tampon package and continuous process for making the package. Heat seals, preferably hermetic longitudinal and cross seals, are preferably peelable. The tampon is sealed under sufficient negative pressure to snugly retain the tampon in place without crushing or misshaping the tampon, yet without bursting the package under normal external pressures realized during storage. The tampon package will remain sealed during normal wear and tear, yet is easily opened when desired by peeling the seals.

15 Claims, 1 Drawing Sheet

TAMPON PACKAGE AND METHOD FOR MAKING SAME

BACKGROUND OF THE INVENTION

The invention relates to a tampon package. More specifically, the invention is directed to a hermetically sealed, moisture-proof, peelable package for storing tampons and for ease of opening.

Tampons are commonly packaged using a paper wrapping. Such wraps allow air and moisture to seep through and contaminate the tampon.

It is also known to package tampons in plastic. However, known packages use positive pressure. If pressure is applied to the tampon, the package can burst open. Such packages also may use perforated ends which can wear apart over time.

Accordingly, it would be advantageous, and it is an object of the invention to provide: a tampon package which is sealed in a negative atmosphere to prevent bursting of the package from external pressure; which provides a hermetically sealed, moisture-proof package; and which provides a peelable package whose openings will not wear open over a reasonable storage time.

It would also be advantageous, and is another object of the invention, to provide a continuous process for packaging tampons in this manner.

DEFINITION OF CLAIM TERMS

The following terms are used in the claims of the patent as filed and are intended to have their broadest meaning consistent with the requirements of law.

"Hermetic seal" or "hermetically sealed" means a seal that will exclude air and will be leakproof at normal temperatures and atmospheric pressure to the extent the thermoplastic materials used permit.

"Peelable" refers to a seal which may be readily manually broken by a consumer.

Where alternative meanings are possible, the broadest meaning is intended. All words used in the claims are intended to be used in the normal, customary usage of grammar and the English language.

SUMMARY OF THE INVENTION

The objects mentioned above, as well as other objects, are solved by the present invention, which overcomes disadvantages of prior art packages and packaging methods, while provided new advantages not previously obtainable.

In one embodiment of the present invention, a sealed tampon package is provided using a length of thermoplastic material entirely enclosing the tampon and formed into a wrapper. The wrapper may include top and bottom web portions. The bottom web portion may be comprised of an extensible, thermoformed material. The wrapper preferably includes two opposed longitudinal seals formed along its length and two opposed cross-seals. These seals may be heat seals, and preferably are hermetic heat seals. The seals may be formed by applying pressure at sealing zones located at opposed edges on the package and heating the sealing zones to a temperature and for a time sufficient to form longitudinal and cross seals that are hermetic around the entire periphery of the package. The hermetically sealed, individually wrapped tampon is under negative pressure, such as in the range of 8–20 inches of Mercury, and more preferably in the range of 10–15 inches of Mercury, in an amount sufficient to retain the tampon snugly within the package without crushing or misshaping the tampon. At least one of the cross-seals and/or the longitudinal seals is peelable, preferably without delamination of the thermoplastic material. The peelable seals preferably have a peel strength in the range of 600–800 grams/inch of width.

Various alternative film materials may be manufactured and formulated for use as the package material. For example, the thermoplastic film may consist of an extruded film, or a solution cast or calendered material. Further, the top web portion may be made of a linear low density polyethylene material comprising an ethylene vinyl acetate/polyisobutylene blend, while the bottom web portion may be made of a nylon/low density polyethylene blend.

In an alternative embodiment, the cross-seals may include one or more notches to facilitate opening of the package. Tear tape may also be used to facilitate package opening.

In another embodiment, the package may include a flow-through style wrapper in which negative pressure on the tampon is provided using a gas flush technique.

In another preferred embodiment, the invention consists of a continuous process for hermetically packaging a tampon, in which a continuous web of heat-sealable thermoplastic material is formed into a first wrapper which entirely encloses the tampon. As the web is continuously moved in a forward direction, portions of the web periphery surrounding the tampon are heated and pressured in a sufficient amount to form hermetic longitudinal and cross seals so that the tampon is entirely surrounded by the hermetically sealed plastic web to form a hermetically sealed package. The hermetic seals are formed in a continuous manner as the web is moved forward, and are peelable. Negative pressure is applied to the tampon within the package in the range of about 8–20 inches of Mercury. Negative pressure may be applied using a gas flush technique. Preferably, the peel strength of the peelable seals is in the range of 600–800 grams/inch of width.

In an alternative embodiment, the tampon may first be packaged in a second, inner wrapper, which may be made of a paper-based material, prior to being packaged within the first wrapper.

BRIEF DESCRIPTION OF THE DRAWINGS

The novel features which are characteristic of the invention are set forth in the appended claims. The invention itself, however, together with further objects and attendant advantages thereof, will be best understood by reference to the following description taken in connection with the accompanying drawings, in which:

DETAILED DESCRIPTION OF THE PREFERRED EMBODIMENTS

Set forth below is a description of what is currently believed to be the preferred embodiment and/or best example of the invention claimed. Future and present alternatives and modifications to this preferred embodiment are contemplated. Any alternatives or modifications which make insubstantial changes in function, in purpose, in structure or in result are intended to be covered by the claims of this patent.

Figure 1:
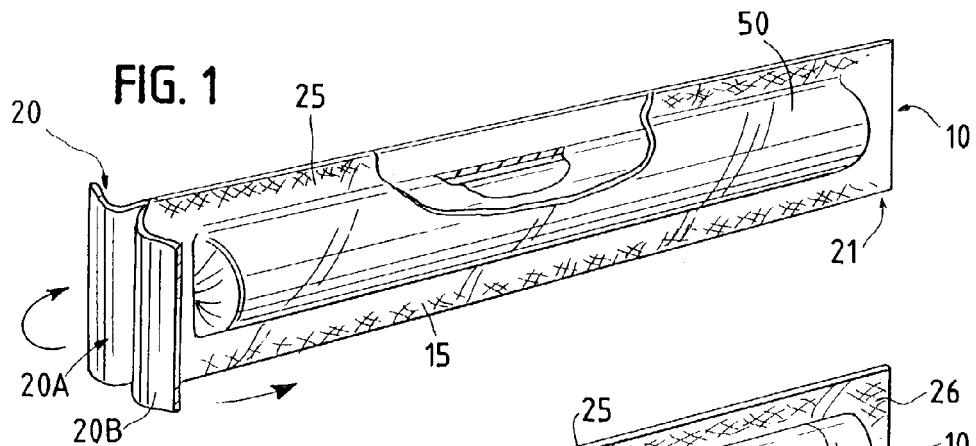
FIGS. 1—4 are side perspective views of various embodiments of the tampon package invention.

In accordance with a preferred embodiment of the invention, a packaged tampon, generally referred to as 10, is shown in FIG. 1. Package 10 preferably incorporates the advantages of the invention described above, and may include an extensible, thermoformed, longitudinal bottom web 15 designed to snugly hug the tampon, a top web 17 which forms the opposing longitudinal side of the package, and opposing ends 20, 21. One of the webs, preferably the top web, may be colorized if desired. A peelable heat seal, preferably a hermetic seal, may be provided. Use of hermetic longitudinal seals 25 and hermetic cross-seals 26 will insure that the tampon is entirely, hermetically enclosed within the package.

"Peelable" refers to a seal which may be readily, manually broken by the consumer; preferably no rupturing or tearing of the film occurs during peeling, though this is not a requirement of the invention. Unsealed opposing flaps 20A, 20B may be provided at one end of the package to facilitate peeling open the heat sealed package. At least one of the cross-seals and/or the longitudinal seals is preferably peelable without delamination of the thermoplastic material. A seal may also be provided which is peelable by delaminating layers of film in a lamination, i.e., the bond strengths in the lamination are designed to give way when subjected to peel force. Preferably, the opposing ends intersect in a hermetic seal which is sufficiently strong so that mere storage, normal handling or the passage of time will not wear away the seal and cause it to unintentionally open. The hermetic seal may be adhesive (i.e., referring to a seal failure mode in which a film sealant layer(s) separate from a base or substrate film layer) or cohesive (i.e., referring to a seal failure mode in which portions of a film sealant layer(s) separate from itself/themselves) in nature. Cohesive failure peel seals may be created using polyisobutylene, which prevents the plastics at the sealing interfaces from tightly commingling and allows them to peel apart without tearing film. Cohesive seals may, when peeled, leave a discoloration, which may or may not be desirable. The hermetic seal preferably falls within the following negative pressure ranges: 8–20, and more preferably 10–15, inches of Mercury as determined through visual observation in a bell jar. Preferably, the tampon is sealed in a negative atmosphere sufficient to prevent bursting of the package from external pressure, and also sufficient to maintain a hermetic seal, yet not so strong as to constrict or misshape the tampon. 23–25 inches of Mercury was determined to be excessive negative pressure which crushed the tampon. The peel strength of the heat seals is preferably in the range of 600–800 grams/inch of width.

Figure 2:
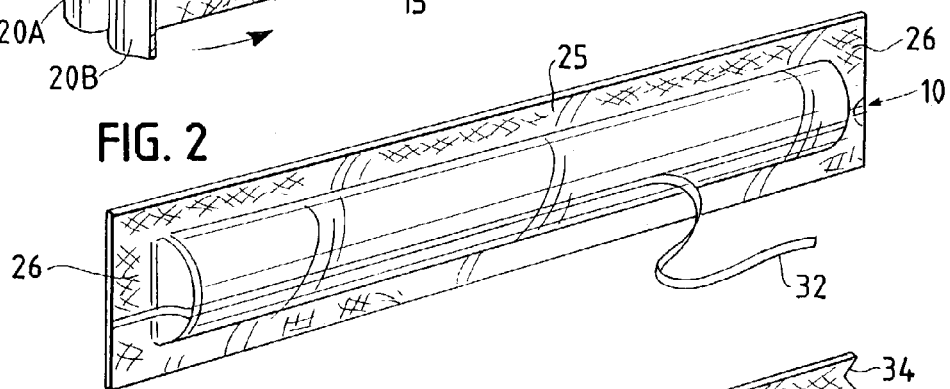
Figure 3:
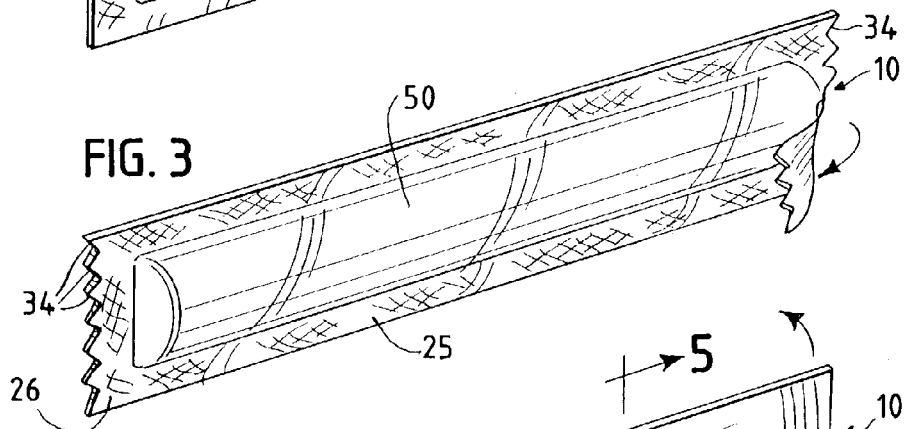

In an alternative embodiment, an easy-open feature may be provided. Thus, as shown in FIG. 2, Zip opening tear tape 32 may be employed to facilitate opening of package 10. One or more tear notches may be also be provided, as shown in FIG. 3, designed to tear linearly, and may be used with or without tear tape.

In yet another alternative embodiment, a flow-through style wrapper using vacuum or gas flush may be provided. For example, a nitrogen-carbon dioxide gas mixture may be introduced into the tube, such that as the carbon dioxide escapes from the film (the nitrogen, with its larger molecules, will do so more slowly over time), the film will fit snugly against the tampon. The degree of snugness can be modified given the gas mixture and the film permeation rates.

Figure 4:
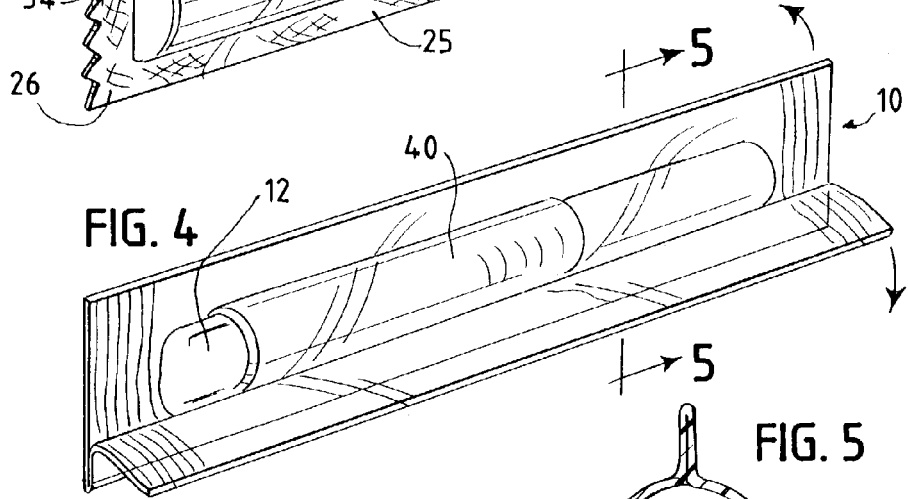
Figure 5:
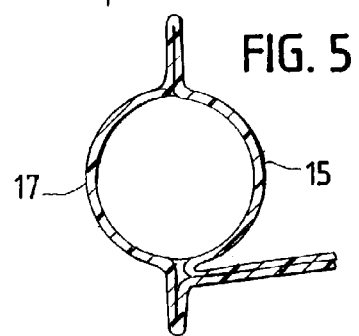
FIG. 5 is a sectional view along reference line 5—5 of FIG. 4.

Alternatively, as shown in FIG. 4, the tampon 12 may be packaged in a paper, "inner" wrapper 40, which is then packaged in a plastic "outer" wrapper as described above. The inner wrapper is not a necessary part of the invention, however.

One film material 50 suitable for forming a top web and providing a peelable seal is 48 BOPet (biaxially oriented polyester) adhesive, 2 mil. LLDPE (linear low density polyethylene, EVA (ethylene vinyl acetate)-PIB (polyisobutylene) blend), coextrusion. EVA/PIB blend is used to provide peel seal properties. Other suitable films for forming a top web and providing a peelable seal include:

48 BOPet/7#LDPE/1.5 mil LLDPE (EVA-PIB blend) coextrusion, where LDPE is low density polyethylene 60 BON/adhesive/2 mil LLDPE (EVA-PIB blend) coextrusion, where BON is biaxially oriented nylon 60 BON/7# LDPE/1.5 mil. LLDPE (EVA-PIB blend) coextrusion 80 BOPP/adhesive/2 mil. LLDPE (EVA-PIB blend) coextrusion, where BOPP is biaxially oriented polypropylene 80 BOPP/7# LDPE/1.5 mil. LLDPE (EVA-PIB blend) coextrusion A thermoformable bottom web may be provided using one of these films, for example:

3–3.5 mil. Nylon/tie/LLDPE coextrusion

2–2.5 mil. Nylon/adhesive/1 mil. LLDPE

2–2.5 mil. formable PET/adhesive/1 mil. LLDPE, where PET is polyester.

While non-oriented substrate film layers are currently preferred (to avoid additional film processing steps, and also because cast films tend to be lower cost), there may be some advantage in a particular application to using an oriented film, which may be stronger than a non-oriented film.

Various additives may be provided to the film for different purposes. Processing aids such as slip and antiblock additives may also be used as needed. Slip or coefficient of friction (COF), the measure of how easily or difficult a film surface slips upon itself. Typically, films with COFs in the range of 0.1 to 0.3 (high to medium slip) are suitable for high speed automatic wrapping machines.

Of course, those of ordinary skill in the art will realize that other film formulations can be used to accomplish the general objectives of the present invention. Potential film substrates may include polyethylene and its variants (such as EVA (ethylene vinyl acetate), EMA (ethylene methyl acrylate), EEA (ethylene ethyl acrylate), HDPE, LDPE, LLDPE, linear LDPE, and metallocene polyethylenes), polypropylene, paper, nylon, cellophane, polyester, aluminum foil, polystyrene or acrylonitriles. Potential sealant layer compositions may include polyethylene and its variants, as well as waxes and other food-safe adhesives or coatings such as ionomers, polybutylene, acid-modified EVA, EMA, tackifiers such as terpenes, synthetic waxes and polyisobutylene.

Film processing techniques that can be utilized to provide packaging films useful with the present invention include, but are not limited to, extrusion, coextrusion, extrusion coating, lamination and dry lamination, for example.

It will be understood by those of ordinary skill in the art that the efficacy of a heat seal is a function of dwell time, sealing temperature and sealing pressure. It will also be understood that the particulars of such time, temperature and pressure will vary depending upon such variables as the film selected, the desired speed, the food item selected, the sealing equipment used, and the desired seal character.

Persons of ordinary skill in the art will understand that, typically, packages of the present invention will be made using a horizontal thermoform machine, as well known in the art. However, it is also understood that the present invention may be adapted for use with vertical fill-and-form machines, as well.

Those of ordinary skill in the art will appreciate that the parameters involved in food packages may differ from non-food packages in some respects. Food packages generally require low oxygen and moisture permeation rates, i.e., 1 cc or less of oxygen per 100 sq. inches/24 hours, and 1 gram or less of moisture per 100 sq. inches/24 hours. Hermetically sealed food packages are an obvious preference to maintain low oxygen and moisture quantities within the package throughout its handling and distribution cycle. Hermetic seals provide sanitary advantages for tampon packaging, as well. Direct contact food packaging materials must meet FDA regulations spelled out in Rule 21 of the Code of Federal Regulations. Finally, the design of food packaging equipment must incorporate features to minimize potential for food contamination, i.e., stainless steel food contact surfaces and disassembling features to assure effective cleaning.

The above description is not intended to limit the meaning of the words used in the following claims that define the invention. Rather, it is contemplated that future modifications in structure, function or result will exist that are not substantial changes and that all such insubstantial changes in what is claimed are intended to be covered by the claims.

I claim:

1. A hermetically sealed, moisture-proof tampon package which resists inadvertent opening and maintains the package integrity, thereby preventing damage and contamination to the tampon, comprising:
   a length of thermoplastic material entirely enclosing the tampon, the thermoplastic material formed into a flexible wrapper;
   the wrapper having two opposed hermetic longitudinal seals formed along its length and two opposed hermetic cross-seals, the seals being formed by applying pressure at sealing zones located at opposed edges on the package and heating the sealing zones to a temperature and for a time sufficient to form longitudinal and cross seals that are hermetic around the entire periphery of the package;
   wherein a hermetically sealed individually wrapped tampon is produced which is under negative pressure sufficient to retain the tampon snugly within the package without crushing or misshaping the tampon; and
   wherein at least one of the cross-seals and the longitudinal seals are manually peelable.

2. The tampon package of claim 1, wherein the seals are peelable without delamination of the thermoplastic material.

3. The tampon package of claim 1, wherein the negative pressure is in the range of 8–20 inches of Mercury.

4. The tampon package of claim 3, wherein the negative pressure is in the range of 10–15 inches of Mercury.

5. The tampon package of claim 1 wherein the peelable seals have a peel strength in the range of 600–800 grams/inch of width.

6. The tampon package of claim 1, wherein the wrapper comprises top and bottom web portions, wherein the bottom web portion comprises an extensible, thermoformed material.

7. The tampon package of claim 6, wherein the top web portion comprises a linear low density polyethylene material comprising an ethylene vinyl acetate/polyisobutylene blend.

8. The tampon package of claim 6, wherein the bottom web portion comprises a nylon/low density polyethylene blend.

9. The tampon package of claim 1 wherein at least one of the cross-seals includes one or more notches to facilitate opening of the package.

10. The tampon package of claim 1, the package further comprising tear tape to facilitate its opening.

11. The tampon package of claim 1, wherein at least one of the longitudinal sides of the package comprises an extensible, thermoformed plastic material.

12. The tampon package of claim 1, wherein the package comprises a flow-through wrapper and negative pressure is provided using a gas flush technique.

13. The tampon package of claim 1, wherein the thermoplastic film comprises an extruded film.

14. The tampon package of claim 1, wherein the thermoplastic film comprises a solution cast or calendered material.

15. A sealed, moisture-proof tampon package which resists inadvertent opening and maintains the package integrity, thereby preventing damage and contamination to the tampon, comprising:
   a length of thermoplastic material entirely enclosing the tampon, the thermoplastic material formed into a flexible wrapper;
   the wrapper having two opposed longitudinal heat seals formed along its length and two opposed cross-seals comprising heat seals, the heat seals being formed by applying pressure at sealing zones located at opposed edges on the package and heating the sealing zones to a temperature and for a time sufficient to form longitudinal and cross heat seals around the entire periphery of the package;
   wherein a heat sealed individually wrapped tampon is produced which is under negative pressure sufficient to retain the tampon snugly within the package and to cause the package to substantially conform to the shape of the tampon without crushing or misshaping the tampon; and
   wherein at least one of the cross-seals and the longitudinal seals is manually peelable.

* * * * *